United States Patent
Lakner et al.

(10) Patent No.: US 6,413,504 B1
(45) Date of Patent: Jul. 2, 2002

(54) ALPHA-ARYLATED CINNAMIC ESTERS AND 1,4-BIS(ALPHA-CARBOXYL-BETA-STYRYL)BENZENE ESTERS AN UV-BLOCKING AGENTS

(75) Inventors: Frederick J. Lakner, San Antonio, TX (US); Bishwajit Nag; Partha Neogi, both of Fremont, CA (US)

(73) Assignee: Calyx Therapeutics, Inc., Hayward, CA (US)

( * ) Notice: Subject to any disclaimer, the term of this patent is extended or adjusted under 35 U.S.C. 154(b) by 0 days.

(21) Appl. No.: 09/610,098

(22) Filed: Jun. 30, 2000

(51) Int. Cl.⁷ .................................................. A61K 7/44
(52) U.S. Cl. ........................ 424/60; 560/81; 424/400; 424/401
(58) Field of Search ............................ 560/81; 424/59, 424/60, 400, 401

(56) References Cited

U.S. PATENT DOCUMENTS 3,275,520 A * 9/1966 Strobel et al.
5,457,226 A * 10/1995 Gygax et al. .................. 560/75
5,587,150 A * 12/1996 Deflandre et al. ............. 424/59
5,770,620 A   6/1998 Mjalli et al.

OTHER PUBLICATIONS

The Merck Index, 11th Edition, Merck and Co, 1989, p. 1157 Aldrich Catalog, Handbook of Fine Chemicals, 1996–97, p. 1157.*
He et al, Chinese Chemical Letters, vol. 8, No. 10, pp. 883–884.*
Pettit et al, Juornal of Natural Products, vol. 51, No. 3, pp. 517–527.*

* cited by examiner

Primary Examiner—Gary Geist
Assistant Examiner—Hector M Reyes
(74) Attorney, Agent, or Firm—Pillsbury Winthrop LLP

(57) ABSTRACT

Compounds of the structure

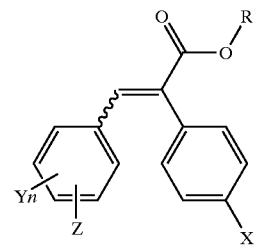

wherein R and R' are H, alkyl or aryl and each Z, X, Y and X' is H, acylamino, acyloxy, alkanoyl, alkoxycarbonyl, amino, alkyl, alkoxy, hydroxy, alkylamino, dialkylamino, arylamino, alkylaryl, diarylamino, halo, carboxyl or cyano; and Z can also be

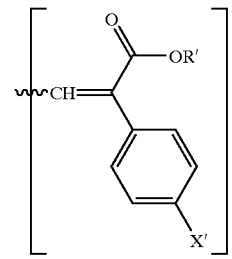

are effective UV blockers.

14 Claims, 1 Drawing Sheet

| COMPOUND | MOLAR ABSORPTION | |
|---|---|---|
| | 305 nm | 350 nm |
| Ic | 1318 | 1355 |
| HMB | 886 | 441 |
| Ib | 1695 | 430 |
| Ia | 1073 | 268 |
| CDA | 1334 | 220 |
| PMC | 2252 | 39 |
| DAB | 2619 | 10 |

| COMPOUND | MOLAR ABSORPTION | |
|---|---|---|
| | 305 nm | 350 nm |
| Ic | 1318 | 1355 |
| HMB | 886 | 441 |
| Ib | 1695 | 430 |
| Ia | 1073 | 268 |
| CDA | 1334 | 220 |
| PMC | 2252 | 39 |
| DAB | 2619 | 10 |

ALPHA-ARYLATED CINNAMIC ESTERS AND 1,4-BIS(ALPHA-CARBOXYL-BETA-STYRYL)BENZENE ESTERS AN UV-BLOCKING AGENTS

BACKGROUND OF THE INVENTION

The present application is directed to novel blockers of ultraviolet radiation formed by Perkin condensation of aromatic aldehydes with alpha-aryl acetic acids, followed by esterification with an alcohol.

Ultraviolet-blocking agents may be either inorganic or organic compounds. Inorganic UV blocking agents are effective by virtue of their reflective properties, while organic blocking agents absorb UV radiation and convert it to other forms of energy, mostly heat. Many organic compounds have been prepared and used as ingredients for sunscreening products. Compounds used for this purpose must be stable, nontoxic, and amenable to formulation.

The UV radiation permeating the earth's atmosphere has wavelengths ranging from about 290 nm to 400 nm. The radiation with wavelengths ranging from 290 to 320 nm is designated UVB radiation and is commonly referred to as the "burning rays." The radiation with wavelengths ranging from 320 to 400 nm is designated UVA radiation and is commonly referred to as the "tanning rays." Overdoses of either kind can cause inflammation, suppress the immune system, and damage DNA.

SUMMARY OF THE INVENTION

Compounds of the formula I:

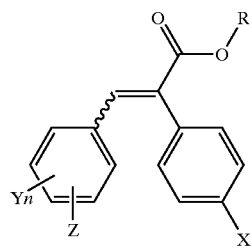

wherein R is H, linear or branched alkyl of 1 to 20 carbon atoms or aryl of 5 to 20 carbon atoms; Z, X and Y are independently H, acylamino of 1 to 20 carbon atoms; acyloxy of 1 to 20 carbon atoms; alkoxycarbonyl of 2 to 20 carbon atoms; amino; linear or branched alkyl of 1 to 20 carbon atoms; linear or branched alkoxy of 1 to 20 carbon atoms; hydroxy; alkylamino of 1 to 20 carbon atoms; dialkylamino of 2 to 40 carbon atoms; arylamino of 5 to 20 carbon atoms; alkylaryl of 6 to 40 carbon atoms; diarylamino of 10 to 40 carbon atoms; halo, carboxyl, or cyano; n is an integer from 1 to 4, and Z can also be

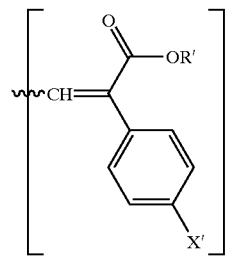

wherein R' is independently selected from the same groups defining R; and X' is independently selected from the same groups defining X;

possess a UV useful absorption spectrum with $\lambda_{max}$ which make them suitable as UV blockers.

A preferred class of compounds includes those in which R is linear or branched alkyl; X is hydroxy; Z and Y are independently H or linear or branched alkoxy. In this class, the compounds wherein X is hydroxy; Y is H, n=2 and Z is alkoxy; and wherein X is hydroxy; $Y_n$ is alkoxy, n=2, and Z is H are particularly preferred.

In the class of compounds where in Z is

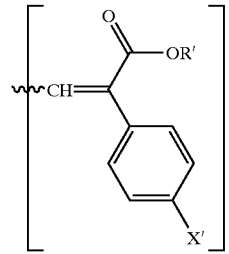

the compounds wherein R' and R are independently linear or branched alkyl; $Y_n$ is hydrogen, n=2; and X' and X are hydroxy, are preferred. The indication of ∼∼∼ means that the carbon-carbon double bond configuration may be E or Z.

DESCRIPTION OF THE PREFERRED EMBODIMENTS

Figures 1, 2:
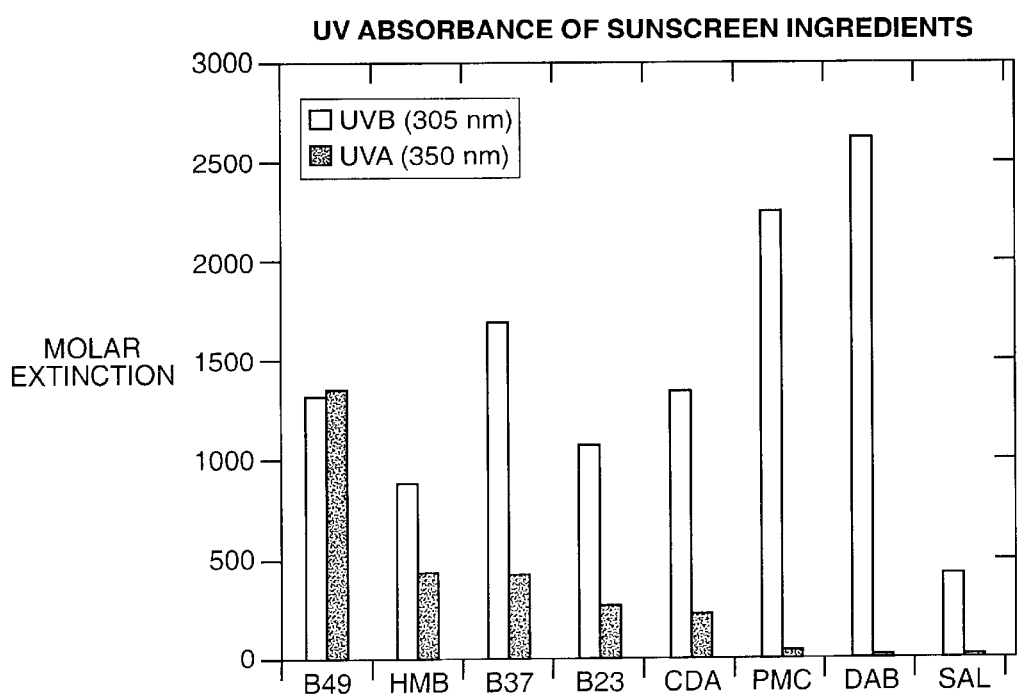
FIG. 1 tabulates the molar absorbance of various tested sunscreen ingredients at 305 nm (UVB radiation) and at 350 nm (UVA radiation).
FIG. 2 shows graphically the molar extinction coefficients of the tested sunscreen ingredients at 305 nm (UVB radiation) and at 350 nm (UVA radiation)

Compounds of formula I have been found which possess a UV absorption spectrum with a lambda (max) in the UVB radiation range (290–320 mm). Some of these compounds have an absorption spectrum which extends even into the UVA range which make them useful UVA and UVB blockers as well.

In the above formulas, linear and branched alkyl include, but are not limited to, methyl, ethyl, n-propyl, i-propyl, n-butyl, sec-butyl, t-butyl, 2-ethyl-hex-1-yl and the like.

Aryl includes aromatic rings such as phenyl, naphthyl, anthracyl, and the like.

Acylamino includes RCONH— wherein R is alkyl or aryl as defined above.

Acyloxy includes RCOO— wherein R is hydrogen, alkyl or aryl as defined above.

Alkanoyl includes the group

wherein R is hydrogen, alkyl or aryl as defined above.

Alkoxycarbonyl includes the group

wherein R is alkyl as defined above.

Alkoxyl includes methoxy, propoxy, isopropoxy, and the like.

The groups alkylamino, dialkylamino, arylamino, alkylaryl and diarylamino include the definitions of alkyl and aryl as defined above.

Halo includes fluoro, bromo, iodo, chloro.

In general, the compounds of the invention may be prepared as follows:

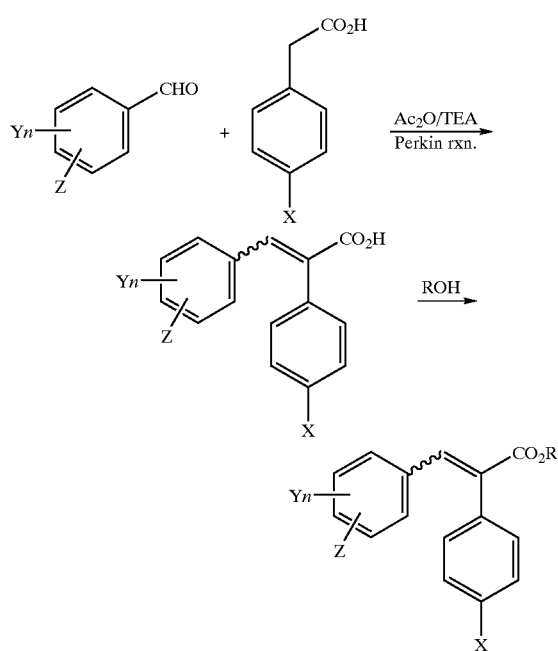

Compounds similar to Ic may be made from dialdehyde starting material.

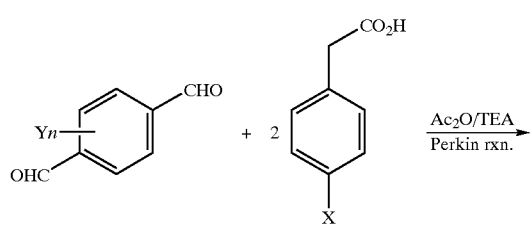

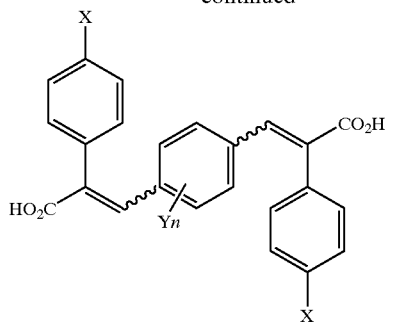

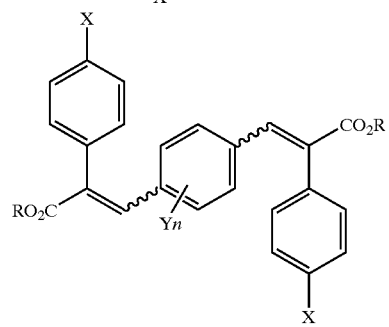

The compounds of the invention are useful as UV blockers. They may be utilized topically as a spray, oil, ointment, and the like with pharmaceutically acceptable carriers. As a topical agent, the amount of active ingredient in the carrier may be determined empirically by those of ordinary skill in the art. The compounds will typically be effective blockers of UVB radiation (290–320 nm) which is dangerous skin burning radiation. Some of the compounds will also be effective blockers of UVA radiation (320–400 nm) which is characterized as skin-tanning, but may nevertheless be harmful.

The compounds may also be used in industrial materials to protect from UV damage. For example, the compounds may be mixed into plastics for use in automobile parts, upholstery, and the like.

Compounds where R and R' are independently linear or branched alkyl of 1 to 20 carbon atoms and X and X' are hydroxy are particularly preferred. The groups R and R' are preferably methyl or 3-octyl.

The groups Z and Y are preferably hydrogen or linear or branched alkoxy of 1 to 20 carbon atoms. Compounds where Y is H and Z is methoxy or $Y_i = Y_2 =$ methoxy and Z is H are preferred.

In the following examples, the 2-ethylhexyl ester Ia and a para-methoxy derivative Ib were synthesized for comparison to other esters currently in use as sunscreen agents. Another preferred compound, Ic, was synthesized for testing.

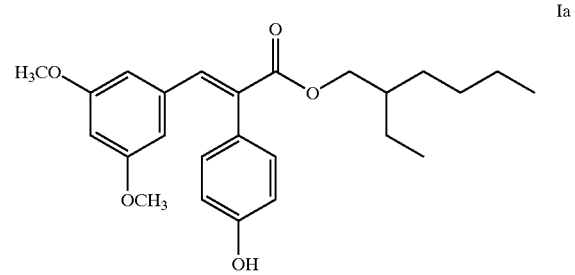

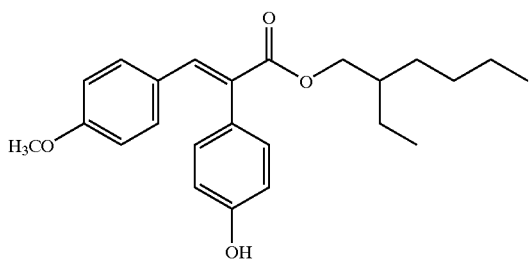

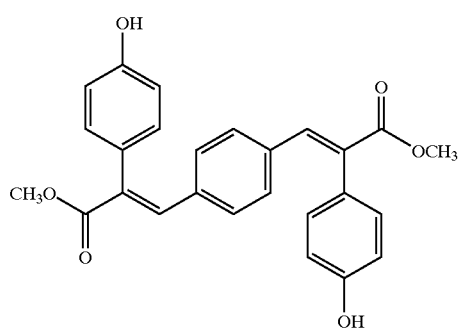

C. Concentrated HCl (20 mL) was added to the reaction mixture slowly in 5 minutes, keeping temperature between 20–30° C. The light yellow precipitate obtained was filtered (wet~10 g) and dissolved in $CH_2Cl_2$ (150 mL). Methylene chloride solution was extracted with 2M aqueous NaOH solution (3×75 ml). The aqueous layers were pooled together and washed with $CH_2Cl_2$ (50 mL). The aqueous layer thus obtained was acidified, maintaining a temperature at 25–30° C., with concentrated HCl (~40 mL) to pH 1 and stirred for 2 hours at room temperature. The product was filtered and washed with ice cold water (2×20 mL) to give crude product (~11 g). The crude product was recrystallized from EtOH—$H_2$) (4:1, 50 mL) mixture to yield white crystals of 1,(3.20 g, 35.5%).

A mixture of 1 (1.0 g, 3.2 mM), 2-ethyl hexan-1-ol and p-toluenesulfonic acid (250 mg) were taken in toluene (5 mL) and refluxed for 7 hours with continuous removal of water, diluted with ethyl acetate and washed with saturated bicarbonate solution. The organic layer was dried on anhydrous magnesium sulfate and evaporated. The crude product was purified by chromatography on $SiO_2$ gel (Hexanes: EtOAc-4:1). UV (EtOH) $\lambda_{max}$ 228, 286, 410 nm; $^1$HNMR ($CDCl_3$): 7.69 (s, 1H), 7.09 (d, J=8.8 Hz, 2H), 6.81 (d, J=8.8 Hz, 2H), 6.32 (t, J=2 Hz, 1H), 6.25 (d, J=2 Hz, 2H), 4.10 (d, J=5.2 Hz, 2H), 3.56 (s, 6H), 1.57–0.84 (m, 15H).

EXAMPLE 1

Synthesis of Compound Ia

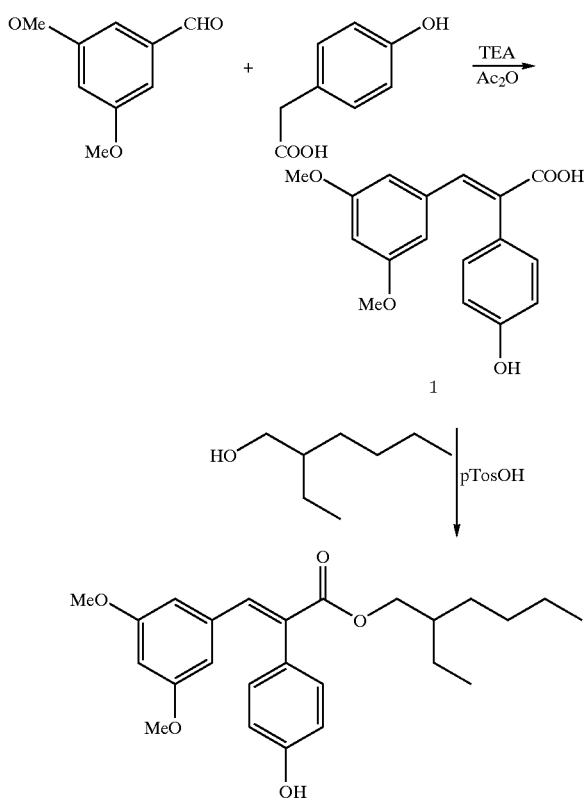

EXAMPLE 2

Synthesis of Compound Ib

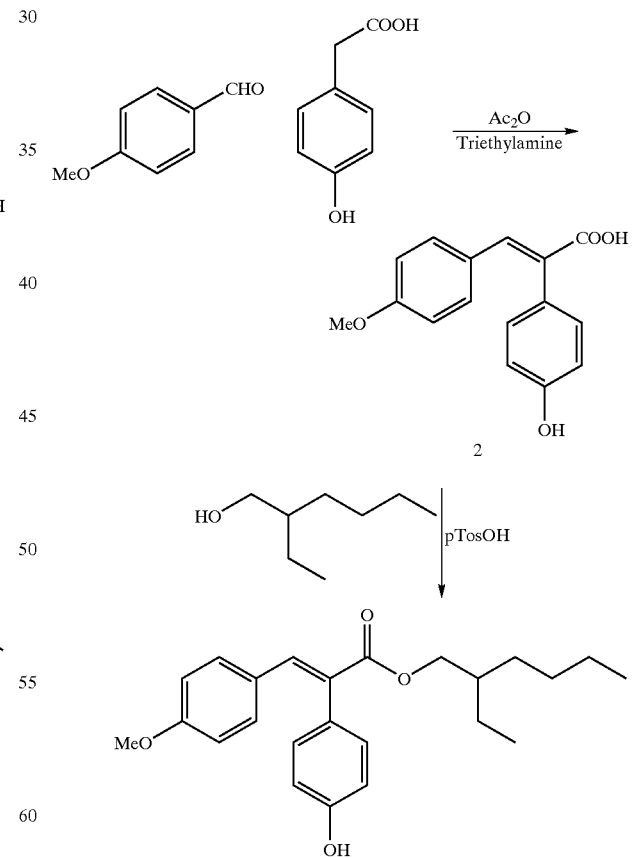

To a mixture of 3,5-dimethoxybenzaldehyde (5.0 g, 30 mM) and p-hydroxyphenyl acetic acid (4.57 g, 30 mM) under nitrogen atmosphere was added acetic anhydride (10 ml) and triethylamine (4.2 ml, 30 mM). After being stirred at 130–140° C. for 18 hours, the mixture was cooled to 20°

To a mixture of 4-methoxybenzaldehyde (4.48 g, 33 mM) and p-hydroxyphenyl acetic acid (5.0 g, 33 mM) under nitrogen atmosphere was added acetic anhydride (10 mL) and triethylamine (7.3 mL, 53 mM). After being stirred at 130–140° C. for 2 hours, the mixture was poured in ice and 5% acqueous HCl (100 mL) was added. The precipitate obtained was taken up in 2N NaOH (150 mL) and filtered through Celite. Filtrate was acidified with concentrated HCl solid precipitated was washed with water. Repeated crystallization from MeOH— water mixture yielded pure 2, 2.44 g.

A mixture of 2 (1.92 g, 7.1 mM), 2-ethyl hexan-1-ol (1.67 g, 12.8 mM) and p-toluenesulfonic acid (0.50 g) were taken in toluene (10 mL) and refluxed for 2.5 hours with continuous removal of water, diluted with ethyl acetate and washed with saturated bicarbonate solution followed by brine. The organic layer was dried on anhydrous magnesium sulfate and evaporated. The crude product was purified by chromatography on $SiO_2$ gel (Hexanes: EtOAc-4:1). UV (EtOH) $\lambda_{max}$ 227, 300; $^1$HNMR (CDCl$_3$): 7.75 (s, 1H), 7.06 (d, J=8.8 Hz, 2H), 7.03 (d, J=8.8 Hz, 2H), 6.81 (d, J=8.8 Hz, 2H, 6.69 (d, J=8.8 Hz, 2H), 4.09 (d, J=6.0 Hz, 2H), 3.75 (s, 3H), 1.58–0.83 (m, 15H).

EXAMPLE 3

Synthesis of Compound Ic

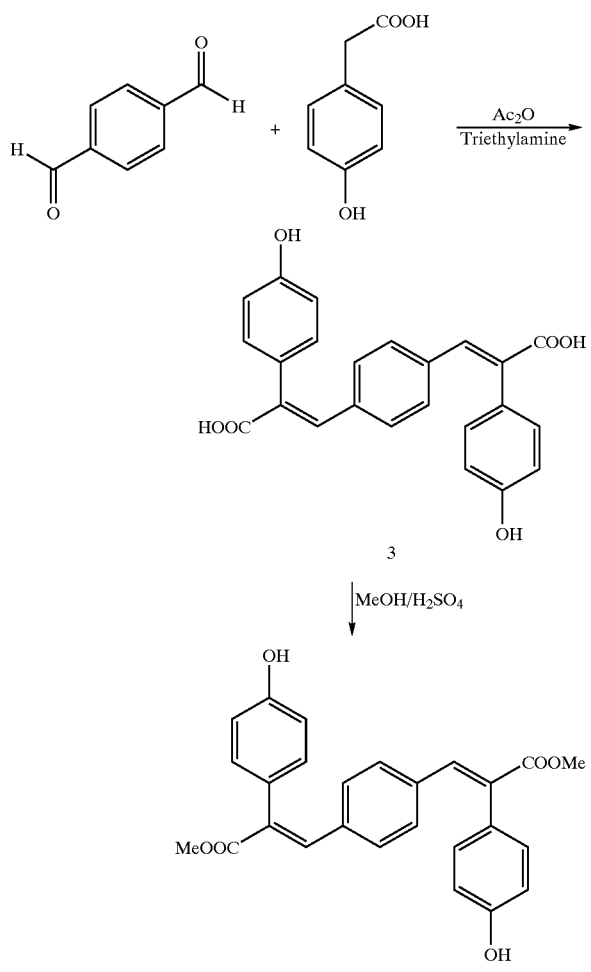

To a mixture of terephthaldicarboxaldehyde (2.0 g, 14.9 mM) and p-hydroxyphenyl acetic acid (4.57 g, 30 mM) under nitrogen atmosphere was added acetic anhydride (10 ml) and triethylamine (6.7 mL, 48 mM). After being stirred at 135–140° C. for 2 hours, the mixture was poured in ice and concentrated HCl (20 mL) was added. The precitate obtained was filtered and taken up in 2N NaOH (150 mL). The clear orange solution was acidified with concentrated HCl (30 mL). The yellow solid precipitate was washed with water to yield 3. The product was dried at 50° C. for two days.

Sulfuric acid (1 mL) was added to a suspension of crude product 3, in MeOH and refluxed for 18 hours. The reaction mixture was cooled to room temperature, the solid precipitated was filtered was filtered and washed with fresh methanol. Pale yellow solid obtained was dried overnight at 50° C. to yield 1.3 g of the compound Ic. UV (EtOH) $\lambda_{max}$ 230, 305, 350 nm; $^1$HNMR (DMSO-d$_6$): 9.57(s, 2H), 7.57 (s, 2H), 6.92 (d, J=9.2 Hz, 4H), 6.92 (s, 4H), 6.73 (d, J=9.2 Hz, 4H), 3.67 (s, 6H).

EXAMPLE 4

Compounds Ia, Ib and Ic, were compared to the following commerical sunscreening agents:

HMB: 2-Hydroxy-4-methoxybenzophenone
CDA: 2-Ethylhexyl 2-cyano-3,3-diphenylacrylate
PMC: 2-Ethylhexyl 4-methoxycinnamate
DAB: 2-Ethylhexyl 4-(dimethylamino)benzoate
SAL: 2-Ethylhexyl salicylate The UV spectra were obtained in ethanol for each of these compounds, and their molar extinction coefficients were calculated. The extinction coefficients at 305 nm (UVB) and at 350 nm (UVA) were tabulated and graphed for comparison.

FIGS. 1 and 2 summarize the results of these comparisons of absorption of the active ingredients of sunscreening agents. Ordinarily, as absorption at 305 nm increases, absorption at 350 nm decreases. However, it was found that Compound Ib absorbs well at 350 nm and at 305 nm and Compound Ic absorbs UV radiation almost equally well at 305 nm and 350 nm.

What is claimed is:

1. A sunscreen composition comprising an effective sunscreening amount of a compound of the structure:

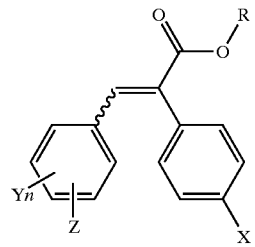

wherein

R is linear or branched alkyl of 1 to 20 carbon atoms; or aryl of 5 to 20 carbon atoms;

Z, X and each Y is independently acylamino of 1 to 20 carbon atoms; acyloxy of 1 to 20 carbon atoms; alkanoyl of 1 to 20 carbon atoms; alkoxycarbonyl of 2 to 20 carbon atoms; amino; linear or branched alkyl of 1 to 20 carbon atoms; linear or branched alkoxy of 1 to 20 carbon atoms; hydroxy; alkylamino of 1 to 20 carbon atoms; dialkyl amino of 2 to 40 carbon atoms; arylamino of 5 to 50 carbon atoms; alkylaryl amino of 6 to 40 carbon atoms; diarylamino of 10 to 40 carbon atoms; halo, carboxyl, or cyano;

n=an integer from 1 to 4;

where Y can also be H;

where Z can also be

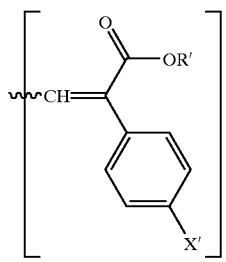

wherein R' is selected from the same groups defining R and X' is selected from the same groups defining X; and configuration at each carbon-carbon double bond is E or Z.

2. The composition according to claim 1 wherein R=linear or branched alkyl of 1 to 20 carbon atoms; X is hydroxy; and Z is alkoxyl of 1 to 20 carbon atoms; and Y is H or alkoxyl of 1 to 20 carbon atoms.

3. The composition according to claim 2 wherein each Y is hydrogen and Z is methoxy.

4. The composition according to claim 2 wherein Z is hydrogen; $Y_1=Y_2=$methoxy.

5. The composition according to claim 4 having the formula:

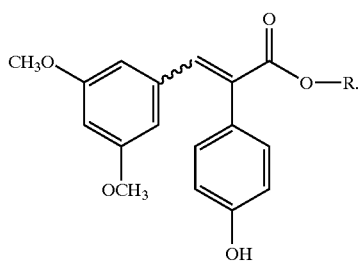

6. The composition according to claim 1 wherein each Y is hydrogen and Z is

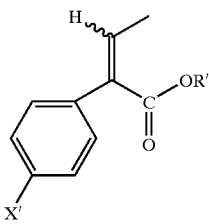

and R' are independently linear or branched alkyl of 1 to 20 carbon atoms; and X' and X are hydroxy.

7. The composition according to claims 6 having the formula:

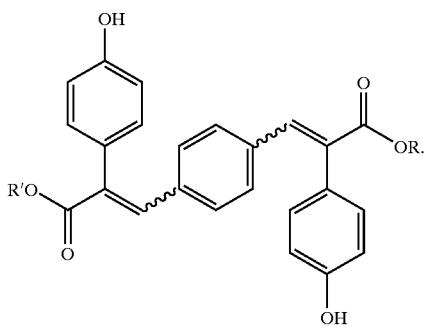

8. The composition according to claim 7 wherein R and R' are methyl.

9. The composition according to claims 3 or 4 wherein R is 2-ethyl-hex-1-yl.

10. A method for protecting the skin from exposure to ultraviolet radiation comprising the step of applying to the skin an effective ultraviolet-blocking amount of a compound according to any of claims 1 to 8.

11. A method for protecting the skin from exposure to ultraviolet radiation comprising the step of applying to the skin an effective ultraviolet-blocking amount of a compound according to claim 9.

12. A method for protecting a material from damage by ultraviolet radiation comprising the step of mixing said material with an effective ultraviolet-blocking amount of a compound according to any of claims 1 to 8.

13. A method for protecting a material from damages by ultraviolet radiation comprising the step of mixing said material with an effective ultraviolet blocking amount of a compound according to claim 9.

14. A sunscreen composition comprising an effective sunscreening amount of a compound according to claim 9 in a pharmaceutically acceptable carrier.

* * * * *